United States Patent
Weber

(10) Patent No.: US 7,364,585 B2
(45) Date of Patent: Apr. 29, 2008

(54) MEDICAL DEVICES COMPRISING DRUG-LOADED CAPSULES FOR LOCALIZED DRUG DELIVERY

(75) Inventor: Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 672 days.

(21) Appl. No.: 10/638,739

(22) Filed: Aug. 11, 2003

(65) Prior Publication Data

US 2005/0037050 A1    Feb. 17, 2005

(51) Int. Cl.
    *A61F 2/06* (2006.01)
(52) U.S. Cl. ............... 623/1.15; 623/1.42; 623/1.43
(58) Field of Classification Search ....... 623/1.42–1.43
    See application file for complete search history.

(56) References Cited

U.S. PATENT DOCUMENTS

| | | | |
|---|---|---|---|
| 5,282,823 A | 2/1994 | Schwartz et al. | 606/198 |
| 5,304,121 A | 4/1994 | Sahatjian | 604/53 |
| 5,693,034 A | 12/1997 | Buscemi et al. | 604/265 |
| 5,700,459 A | 12/1997 | Krone et al. | 424/78.08 |
| 5,702,754 A | 12/1997 | Zhong | 427/2.12 |
| 5,733,925 A | 3/1998 | Kunz et al. | 514/449 |
| 5,855,565 A | 1/1999 | Bar-Cohen et al. | 604/104 |
| 5,893,840 A | 4/1999 | Hull et al. | 604/96 |
| 6,060,534 A | 5/2000 | Ronan et al. | 523/113 |
| 6,096,018 A | 8/2000 | Luzio et al. | 604/500 |
| 6,176,849 B1 | 1/2001 | Yang et al. | 604/265 |
| 6,184,266 B1 | 2/2001 | Ronan et al. | 523/113 |
| 6,261,630 B1 | 7/2001 | Nazarova et al. | 427/2.12 |
| 6,316,522 B1 | 11/2001 | Loomis et al. | 523/105 |
| 6,479,146 B1 | 11/2002 | Caruso et al. | 428/403 |
| 6,699,501 B1 | 3/2004 | Neu et al. | 424/463 |
| 6,833,192 B1 | 12/2004 | Caruso et al. | 428/403 |

(Continued)

FOREIGN PATENT DOCUMENTS

WO    WO 99/47252    9/1999

(Continued)

OTHER PUBLICATIONS

Igor L. Radtchenko et al, "Assembly of Alternated Multivalent Ion/Polyelectrolyte Layers on Colloidal Particles. Stability of the Multilayers and Encapsulation of Macromolecules into Polyelectrolyte Capsules," *Journal of Colloid and Interface Science*, vol. 230, 1999, pp. 272-280.

(Continued)

*Primary Examiner*—Corrine McDermott
*Assistant Examiner*—David A. Izquierdo
(74) *Attorney, Agent, or Firm*—Mayer & Williams PC; David B. Bonham, Esq.; Keum J. Park, Esq.

(57) ABSTRACT

A medical device comprising a plurality of capsules, and a method of administering therapeutic agent to a patient using the same. The capsules further comprise a therapeutic agent and a multilayer polyelectrolyte shell. The medical device is adapted to apply a pressure to the capsules that is greater than or equal to the critical pressure of at least a portion of the capsules, such that therapeutic agent is released from the capsules.

4 Claims, 1 Drawing Sheet

U.S. PATENT DOCUMENTS

| | | | |
|---|---|---|---|
| 2002/0094569 A1 | 7/2002 | Yu et al. | 435/325 |
| 2002/0107330 A1 | 8/2002 | Pinchuk et al. | 525/242 |
| 2002/0187197 A1 | 12/2002 | Caruso et al. | 424/490 |
| 2003/0003272 A1 | 1/2003 | Laguitton | 428/141 |
| 2003/0219909 A1* | 11/2003 | Lally et al. | 436/518 |

FOREIGN PATENT DOCUMENTS

| | | |
|---|---|---|
| WO | WO 99/47253 | 9/1999 |
| WO | WO 00/03797 | 2/2000 |
| WO | WO 00/77281 | 12/2000 |
| WO | WO 01/51196 | 7/2001 |
| WO | WO 01/51196 A1 | 7/2001 |
| WO | WO 02/09864 A1 | 2/2002 |
| WO | WO 02/09865 A1 | 2/2002 |
| WO | WO 02/17888 A2 | 3/2002 |
| WO | WO 2004/014540 A1 | 2/2004 |
| WO | WO 2004/030648 A1 | 4/2004 |
| WO | WO 2004/047977 A1 | 6/2004 |

OTHER PUBLICATIONS

Lars Däbne et al., "Fabrication of Micro Reaction Cages with Tailored Properties," *J. Am. Chem. Soc.*, vol. 123, 2001, pp. 5431-5436.

Edwin W.H. Jager et al., "Microfabricating Conjugated Polymer Actuators," *Science*, vol. 290, Nov. 24, 2000, pp. 1540-1545.

Sergio Moya et al., "Lipid Coating on Polyelectrolyte Surface Modified Colloidal Particles and Polyelectrolyte Capsules," *Macromolecules*, vol. 33, 2000, pp. 4538-4544.

C. Gao et al., "Elasticity of Hollow Polyelectrolyte Capsules Prepared by the Layer-by-Layer Technique," *European Physical Journal E*, vol. 5, 2001, pp. 21-27.

Frank Caruso et al., "Microencapsulation of Uncharged Low Molecular Weight Organic Materials by Polyelectrolyte Multilayer Self-Assembly," *Langmuir*, vol. 16, 2000, pp. 8932-8936.

Igor L. Radtchenko et al., "A Novel Method for Encapsulation of Poorly Water-Soluble Drugs: Precipitation in Polyelectrolyte Multilayer Shells," *International Journal of Pharmaceutics*, vol. 242, 2002, pp. 219-223.

Information from Micromuscle.com website.

Capsulation product literature. 2002.

Catalogue of Certificate Reference Materials 2000-2001. Chemmea Bohemia s.r.o. www.labo.cz/chemmea/katalog/pages/particle.htm.

Dimitry G. Shchukin et al., "Micron-Scale Hollow Polyelectrolyte Capsules with Nanosized Magnetic $Fe_3O_4$ Inside," *Materials Letters*, vol. 57, 2003, pp. 1743-1747.

Gleb Sukhorukov et al., "Controlled Precipitation of Dyes into Hollow Polyelectrolyte Capsules Based on Colloids and Biocolloids," *Advanced Materials*, vol. 12, No. 2 (2000), pp. 112-115.

S. Moya et al., "Microencapsulation of Organic Solvents in Polyelectrolyte Multilayer Micrometer-Sized Shells," *Journal of Colloid and Interface Science*, vol. 216 (1999), pp. 297-302.

Alexei A. Antipov et al., "Polyelectrolyte Multilayer Capsule Permeability Control," *Colloids and Surfaces A: Physiochemical and Engineering Aspects 198-200*, 2002, pp. 535-541.

Xingping Qiu et al., "Studies on the Drug Release Properties of Polysaccharide Multilayers Encapsulated Ibuprofen Microparticles," *Langmuir*, vol. 17, 2001, pp. 5375-5380.

S. Moya et al., "Polyelectrolyte Multilayer Capsules Templated on Biological Cells: Core Oxidation Influences Layer Chemistry," *Colloids and Surfaces: A Physicochemical and Engineering Aspects 183-185*, 2001, pp. 27-40.

Igor L. Radtchenko et al., "Incorporation of Macromolecules into Polyelectrolyte Micro- and Nanocapsules Via Surface Controlled Precipitation on Colloidal Particles," *Colloids and Surfaces: A: Physicochemical and Engineering Aspects 202*, 2002, pp. 127-133.

Winky L.W. Hau et al., "Surface-Chemistry Technology for Microfluidics," *J. Micromech. Microeng.*, vol. 13, 2003, pp. 272-278.

Gi-Ra Yi et al., "Ordered Macroporous Particles by Colloidal Templating," *Chem. Mater.*, vol. 13, 2001, pp. 2613-2618.

Alexei A. Antipov et al., "Sustained Release Properties of Polyelectrolyte Multilayer Capsules," *J. Phys. Chem. B*, vol. 105, 2001, pp. 2281-2284.

* cited by examiner

MEDICAL DEVICES COMPRISING DRUG-LOADED CAPSULES FOR LOCALIZED DRUG DELIVERY

FIELD OF THE INVENTION

The present invention relates to medical devices comprising drug-loaded capsules and to methods of drug delivery using the same.

BACKGROUND OF THE INVENTION

Various medical devices have been developed for the delivery of therapeutic agents to the body. In accordance with some delivery strategies, a therapeutic agent is provided within a polymeric matrix coating that is associated with an implantable or insertable medical device, for example, a vascular balloon catheter or a stent. Release of therapeutic agent from the coating of such devices is, in general, governed by simple diffusion processes. In order to administer a large initial drug release after the device is positioned, the matrix is commonly loaded with a large amount of drug, or the device is dipped into a drug solution immediately prior to insertion. Unfortunately, a significant amount of drug may be washed from the surface of the device between initial insertion and ultimate placement of the device. Such premature release introduces a degree of imprecision with respect to the amount of drug that is dispensed at the placement site, and it results in drug administration to regions of the body other than the placement site—a result that becomes more and more undesirable with increasing drug toxicity.

Accordingly, there is presently a need in the art for devices and methods whereby substantial amounts of drug are released only after the medical device is placed at the site of interest. The present invention addresses these and other needs in the art.

SUMMARY OF THE INVENTION

According to a first aspect of the present invention, a medical device is provided that comprises a plurality of capsules. The capsules further comprise a therapeutic agent and a multilayer polyelectrolyte shell. The medical device is adapted to apply a pressure to the capsules that is greater than or equal to the critical pressure of at least a portion of the capsules, such that therapeutic agent is released from the capsules.

In some embodiments, at least a portion of the capsules comprise two or more therapeutic agents. In some embodiments, at least a first portion of the capsules comprise a first therapeutic agent and at least a second portion of the capsules comprise a second therapeutic agent, which may be the same or different from the first therapeutic agent. In these latter embodiments, the first portion of the capsules can have a first critical pressure, and the second portion of the capsules can have a second critical pressure that is greater than the first critical pressure. The medical device can be activated to apply a pressure to the capsules that is greater than or equal to the first critical pressure, such that the first therapeutic agent is released. The medical device can then be further activated to apply a pressure that is greater than or equal to the second critical pressure such that the second therapeutic agent is released. Alternatively, one can choose not to raise the pressure any further and to remove the second therapeutic with the device out of the body. As a result, one or more drugs can be encapsulated in a variety of capsules with a defined distribution in critical pressures, such that the operator is able to choose the amount and/or type of drug to be released in the body by defining the upper pressure limit during the procedure.

In some embodiments, at least a portion of the capsules are disposed at or near the surface of the medical device. For example, at least a portion of the capsules can be attached to the surface of the medical device. As another example, at least a portion of the capsules can be provided within a polymeric layer at or near the surface of the medical device.

Examples of medical devices include catheters and stents. In certain embodiments, a stent is adapted to apply pressure to the capsules in cooperation with an inflatable balloon. In certain embodiments, a stent comprises an electroactive polymer actuator that applies pressure to the capsules. In certain other embodiments, a stent comprises an actuator made out of single wall carbon nanotubes that applies pressure to the capsules. The stent can be, for example, a coronary vascular stent, a cerebral stent, a urethral stent, a ureteral stent, a biliary stent, a tracheal stent, a gastrointestinal stent or an esophageal stent. Where the medical device is a catheter, it can comprise, for example, a balloon or an electroactive polymer actuator or an actuator based on single wall nanotubes for expansion. The catheter can be, for example, a vascular catheter.

A wide range of therapeutic agents can be provided within the capsules, including anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

According to a further aspect of the present invention, a medical procedure is provided that comprises: inserting a medical device such as one of the above devices into a patient; and activating the medical device to apply the a pressure to the capsules such that the therapeutic agent is released from the capsules. Medical procedures include, for example, stent placement procedures, percutaneous transluminal angioplasty procedures, percutaneous transluminal coronary angioplasty procedures, and other vascular procedures.

An advantage of the present invention is that medical devices and methods are provided, wherein premature release of therapeutic agent is minimized or avoided.

Another advantage of the present invention is that medical devices and methods are provided wherein substantially all of the therapeutic agent is released at the intended site of release.

These and other aspects, embodiments and advantages of the present invention will become immediately apparent to those of ordinary skill in the art upon reading the disclosure to follow.

DETAILED DESCRIPTION OF THE INVENTION

Figure 1A:
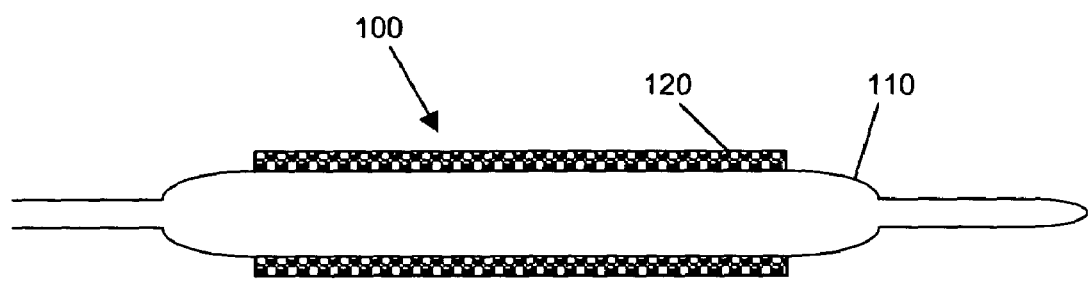
FIG. 1A is a schematic illustration, pre-inflation, of a balloon catheter, in accordance with an embodiment of the invention.

"Drugs," "therapeutic agents," "pharmaceutically active agents," and other related terms may be used interchangeably herein.

In accordance with one aspect of the present invention, an implantable or insertable medical device is provided that comprises a plurality of capsules, which capsules further comprise a therapeutic agent disposed within a multilayer polyelectrolyte shell. The medical device is adapted to apply a pressure to the capsules which is greater than or equal to the critical pressure that is associated with the rupture of at least a portion of the capsules due to deformation, resulting in the release of therapeutic agent.

In many embodiments, the capsules comprise (a) a drug-containing core and (b) a polyelectrolyte multilayer encapsulating the drug-containing core. Such capsules have a number of desirable properties. For example, they permit the encapsulation of a wide variety of therapeutic and other agents, including small molecule pharmaceuticals, polypeptides (e.g., proteins such as enzymes), polynucleotides (e.g., DNA and RNA), and so forth. See, e.g., "Microencapsulation of Organic Solvents in Polyelectrolyte Multilayer Micrometer-sized Shells," S. Moya et al., *Journal of Colloid and Interface Science*, 216, 297-302 (1999).

In addition, drugs can be loaded within these capsules with high precision, for example, in multiples of 0.1 picogram per capsule. See, e.g., "Assembly of Alternated Multivalent Ion/Polyelectrolyte Layers on Colloidal Particles," I. L. Radtchenko et al., *Journal of Colloid and Interface Science*, 230, 272-280 (2000).

Moreover, these capsules can become mechanically unstable upon the application of an external pressure. "Critical pressure" is defined herein as the pressure associated with the rupture of a capsule due to deformation.

The critical pressure associated with spherical capsules has been reported to be predicted by the following formula:

$$\text{Critical pressure} = 4 \cdot \text{Elastic modulus} \cdot (\text{wall thickness} / \text{capsule diameter})^2$$

See C. Gao et al., "Elasticity of hollow polyelectrolyte capsules prepared by the layer-by-layer technique," *European Physics Journal E* 5, 21-27 (2001).

Polyelectrolyte capsules can be prepared using various known layer-by-layer techniques. Layer-by-layer techniques typically involve coating particles dispersed in aqueous media via electrostatic, self-assembly using charged polymeric (polyelectrolyte) materials. These techniques exploit the fact that the particles serving as templates for the polyelectrolyte layers each has a surface charge. This renders the particles water dispersible and provides the charge necessary for deposition of subsequent polyelectrolyte layers. The charge on the outer layer is reversed upon deposition of each sequential polyelectrolyte layer.

Many materials, such as polypeptides and polynucleotides, have an inherent surface charge that is present on particles made from the same. Other materials, for example, many solid and liquid organic compounds, are uncharged. Such materials, however, can nonetheless be encapsulated by layer-by-layer techniques by (a) providing the compound in finely divided form using, for instance, (i) colloid milling or jet milling or precipitation techniques, to provide solid particles, or (ii) emulsion techniques to provide liquid particles within a continuous liquid or gel phase. The particles are then provided with a surface charge, for example, by providing least one amphiphilic substance (e.g., an ionic surfactant, an amphiphilic polyelectrolyte or polyelectrolyte complex, or a charged copolymer of hydrophilic monomers and hydrophobic monomers) at the phase boundary between the solid/liquid template particles and the continuous phase (typically an aqueous phase).

Once a charged template particle is provided, it can be coated with a layer of an oppositely charged polyelectrolyte. Multilayers are formed by repeated treatment with alternating oppositely charged polyelectrolytes, i.e., by alternating treatment with cationic and anionic polyelectrolytes. The polymer layers self-assemble onto the pre-charged solid/liquid particles by means of electrostatic, layer-by-layer deposition, thus forming a multilayered polymeric shell around the cores.

Amphiphilic substances include any substance having hydrophilic and hydrophobic groups. Where used, the amphiphilic substance should have at least one electrically charged group to provide the template particle (solid or liquid) with an electrical charge. Therefore, the amphiphilic substances used also can be referred to as an ionic amphiphilic substances. Amphiphilic polyelectrolytes can be used as amphiphilic substances, for example, polyelectrolytes comprising charged groups as hydrophilic groups as well as hydrophobic groups, e.g. aromatic groups, such as poly(styrene sulfonate) (PSS). Cationic and anionic surfactants can also be used as amphiphilic substances. Cationic surfactants include quaternary ammonium salts ($R_4N^+X^-$), for example, didodecyldimethylammonium bromide (DDDAB), alkyltrimethylammonium bromides such as hexadecyltrimethylammonium bromide (HDTAB), dodecyltrimethylammonium bromide (DTMAB), myristyltrimethylammonium bromide (MTMAB), or palmityl trimethylammonium bromide, or N-alkylpyridinium salts, or tertiary amines ($R_3NH^+X^-$), for example, cholesteryl-3β-N-(dimethyl-aminoethyl)-carbamate or mixtures thereof, wherein $X^-$ is a counteranion, e.g. a halogenide. Anionic surfactants include alkyl or olefin sulfate ($R—OSO_3M$), for example, a dodecyl sulfate such as sodium dodecyl sulfate (SDS), a lauryl sulfate such as sodium lauryl sulfate (SLS), or an alkyl or olefin sulfonate ($R—SO_3M$), for example, sodium-n-dodecyl-benzene sulfonate, or fatty acids ($R—COOM$), for example, dodecanoic acid sodium salt, or phosphoric acids or cholic acids or fluoro-organics, for example, lithium-3-[2-(perfluoroalkyl)ethylthio]propionate or mixtures thereof, where R is an organic radical and M is a counteration.

Polyelectrolytes are polymers having ionically dissociable groups, which can be a component or substituent of the polymer chain. Usually, the number of these ionically dissociable groups in the polyelectrolytes is so large that the polymers in dissociated form (also called polyions) are water-soluble. Depending on the type of dissociable groups, polyelectrolytes are typically classified as polyacids and polybases. When dissociated, polyacids form polyanions, with protons being split off, which can be inorganic, organic and biopolymers. Examples of polyacids are polyphosphoric acids, polyvinylsulfuric acids, polyvinylsulfonic acids, polyvinylphosphonic acids and polyacrylic acids. Examples of the corresponding salts, which are also called polysalts, are polyphosphates, polyvinylsulfates, polyvinylsulfonates, polyvinylphosphonates and polyacrylates. Polybases contain groups which are capable of accepting protons, e.g., by reaction with acids, with a salt being formed. Examples of polybases having dissociable groups within their backbone and/or side groups are polyallylamine, polyethylimine, polyvinylamine and polyvinylpyridine. By accepting protons, polybases form polycations.

Suitable polyelectrolytes according to the invention include those based on biopolymers such as alginic acid, gummi arabicum, nucleic acids, pectins and proteins, chemically modified biopolymers such as carboxymethyl cellulose and lignin sulfonates, and synthetic polymers such as polymethacrylic acid, polyvinylsulfonic acid, polyvinylphosphonic acid and polyethylenimine. Linear or branched polyelectrolytes can be used. Using branched polyelectrolytes can lead to less compact polyelectrolyte multilayers having a higher degree of wall porosity. Polyelectrolyte molecules can be crosslinked within or/and between the individual layers, e.g. by crosslinking amino groups with aldehydes, for example, to increase capsule stability. Furthermore, amphiphilic polyelectrolytes, e.g. amphiphilic block or random copolymers having partial polyelectrolyte character, can be used to reduce permeability towards polar small molecules. Such amphiphilic copolymers consist of units having different functionality, e.g. acidic or basic units, on the one hand, and hydrophobic units, on the other hand, such as styrenes, dienes or siloxanes which can be present in the polymer as blocks or distributed statistically.

By using polyelectrolytes that are degradable, the release of enclosed drug can be further controlled via the degradation of the capsule walls. Examples include polyglycolic acid (PGA), polylactic acid (PLA), polyamides, poly-2-hydroxy-butyrate (PHB), polycaprolactone (PCL) and poly (lactic-co-glycolic) acid (PLGA).

There are essentially no limitations with regard to the polyelectrolytes to be used, as long as the molecules used have sufficiently high charge or/and are capable of binding with the underlying layer via other kinds of interaction, e.g., hydrogen bonds and/or hydrophobic interactions. Suitable polyelectrolytes thus include low-molecular weight polyelectrolytes (e.g., polyelectrolytes having molecular weights of a few hundred Daltons) up to macromolecular polyelectrolytes (e.g., polyelectrolytes of biological origin, which commonly have molecular weights of several million Daltons).

Specific examples of polycations include protamine sulfate polycations, poly(allylamine) polycations (e.g., poly (allylamine hydrochloride) (PAH)), polydiallyldimethylammonium polycations, polyethyleneimine polycations, chitosan polycations, eudragit polycations, gelatine polycations, spermidine polycations and albumin polycations. Specific examples of polyanions include poly(styrenesulfonate) polyanions (e.g., poly(sodium styrenesulfonate) (PSS)), polyacrylic acid polyanions, sodium alginate polyanions, eudragit polyanions, gelatine polyanions, hyaluronic acid polyanions, carrageenan polyanions, chondroitin sulfate polyanions, and carboxymethylcellulose polyanions.

In general, the shape of the final capsule will reflect the shape of the template that is used to form the capsule. Hence, although the capsules are frequently spherical, other less-symmetric capsule shapes including elongated capsules (e.g., using rod shaped templates such as elongated or rod-shaped crystals, chopped extruded polystyrene fibers, and so forth), multifaceted capsules (e.g., using multifaceted templates such as templates with rectangular or square facets, for example, cubes, etc.), flattened capsules (e.g., using flattened near-spherical templates, disk-shaped templates or doughnut-shaped templates, for example, erythrocytes, erythrocyte-shaped polystyrene, etc.), and so forth. Unlike spherical capsules, the critical pressure at which less-symmetric capsules become unstable will vary depending upon the axis along which pressure is applied.

The wall thickness provided by layer-by-layer techniques will frequently range, for example, from 4 to 50 nm. The size of the resulting capsules can vary widely, depending upon the size of the template, and will frequently range, for example, from 50 nanometers to 20 microns in largest dimension, but dimensions well beyond these values are also achievable.

Techniques other than direct encapsulation are also available for encapsulating agents of interest and are preferred in many embodiments. Various techniques take advantage of gradients across the capsule wall to effect precipitation or synthesis of a desired substance within the shell. For example, as a general rule, large macromolecules typically cannot penetrate polyelectrolyte multilayers, while small molecules, on the other hand, can. Accordingly, the presence of macromolecules inside the capsules can lead to a difference in the physico-chemical properties between the inside and the outside of the capsule, for example, providing gradients in pH and/or polarity that can be used to trap materials within the capsules.

For example, in certain instances, macromolecules are provided on the interior of the capsule by forming a double shell polyelectrolyte structure, after which the inner shell is decomposed. For example, capsules have been made by means of layer-by-layer adsorption of oppositely charged polyelectrolytes (i.e., an outer shell of alternating PAH and PSS) on a yttrium$^{3+}$/PSS inner shell, which is further disposed on the surface of a colloidal template particle (i.e., melamine formaldehyde particles). Subsequently, the melamine formaldehyde core is removed, followed by the decomposition of the Yttrium$^{3+}$/PSS inner shell. A solution of a poorly water-soluble drug in an organic solvent (e.g., acetone) can then be mixed with a water suspension of the capsules and diluted with acetone until complete dissolution of the drug is achieved. The organic solvent is then allowed to evaporate. The presence of the free polyelectrolyte molecules in the core results in a higher water concentration within the core, relative to the bulk. Because the concentration of water is higher in the core than in the bulk, the drug precipitates within the core, producing a drug-loaded capsule. Additional information can be found, for example, in "A Novel Method for Encapsulation of Poorly Water-soluble Drugs: Precipitation in Polyelectrolyte Multilayer Shells," I. L. Radtchenko et al., *International Journal of Pharmaceutics*, 242, 219-223 (2002), the disclosures of which is hereby incorporated by reference.

As another example, the selective inorganic synthesis of magnetite ($Fe_3O_4$) inside poly(styrene sulfonate)/poly(allylamine hydrochloride) polyelectrolyte capsules of micron scale as been reported. Micron and submicron sized capsules are made by means of layer-by-layer adsorption of oppositely charged polyelectrolytes (PSS, PAH) on the surface of colloidal template particles (e.g., weakly cross-linked melamine formaldehyde particles having a precipitated PAH-citrate complex) with subsequent degradation of the template core. This leaves free PAH in the core, which creates a pH gradient across the shell. At this point, (a) negatively charged, preformed magnetic particles of sufficiently small size (e.g., $Fe_3O_4$ nanoparticles) can be used to impregnate the capsules whereupon they are held by electrostatic interactions, or (b) magnetic material (e.g., $Fe_3O_4$) can be selectively synthesized inside the core based on the pH gradient and on presence of dissolved PAH in the capsule. The resulting capsules are easily driven by a magnetic field. Additional information can be found, for example, in "Micron-Scale Hollow Polyelectrolyte Capsules with Nanosized Magnetic $Fe_3O_4$ Inside," *Materials Letters*, D. G. Shchukin et al. (in press), the disclosure of which is hereby incorporated by reference.

Further information on the formation of capsules having polyelectrolyte shells can be found, for example, in U.S. patent application 20020187197, WO 99/47252, WO 00/03797, WO 00/77281, WO 01/51196, WO 02/09864, WO 02/09865, WO 02/17888, "Fabrication of Micro Reaction Cages with Tailored Properties," L. Dähne et al., *J. Am. Chem. Soc.*, 123, 5431-5436 (2001), "Lipid Coating on Polyelectrolyte Surface Modified Colloidal Particles and Polyelectrolyte Capsules," Moya et al., *Macromolecules*, 33, 4538-4544 (2000); "Controlled Precipitation of Dyes into Hollow Polyelectrolyte Capsules," G. Sukhorukov et al., *Advanced Materials, Vol.* 12, No. 2, 112-115 (2000), the disclosures of which are hereby incorporated by reference.

Using techniques like those previously discussed, a wide range of drugs can be incorporated into capsules having polyelectrolyte shells. As indicated above, "drugs," "therapeutic agents," "pharmaceutically active agents," "pharmaceutically active materials," and other related terms may be used interchangeably herein. These terms include genetic therapeutic agents, non-genetic therapeutic agents and cells. Therapeutic agents may be used singly or in combination.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms, (p) inhibitors of leukocyte recruitment, such as monoclonal antibodies, (q) cytokines, (r) hormones.

Preferred non-genetic therapeutic agents include paclitaxel, sirolimus, everolimus, tacrolimus, dexamethasone, estradiol, ABT-578 (Abbott Laboratories), trapidil, liprostin, Actinomcin D, Resten-NG, Ap-17, abciximab, clopidogrel and Ridogrel.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and bydrocortisone, (n) lipoxygenase pathway inhibitors such as nordihydroguairetic acid and caffeic acid, (O) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

Beneficial medical devices for use in connection with the above capsules include essentially any medical device that is capable of generating the critical pressure necessary to release an agent from within the capsule.

In many embodiments, the medical device is adapted for placement and expansion in a bodily lumen, such as the lumens associated with the vascular, gastrointestinal, urinary, biliary and pulmonary systems. Examples of medical devices for placement and expansion in such bodily lumens include catheters (for example, urinary or vascular catheters), stents (for example, coronary and peripheral vascular stents, cerebral stents, urethral stents, ureteral stents, renal stents, biliary stents, tracheal stents, gastrointestinal stents and esophageal stents), and other implantable medical devices such as coils, vena cava filters, venous valves, grafts, and so forth. In certain embodiments, the expandable device will further comprise surgical blades to make incisions in the surrounding tissue. For example, The Cutting Balloon™ available from Boston Scientific Corp., Natick Mass., USA, comprises microsurgical blades (known as atherotomes) mounted longitudinally on the outer surface of the balloon.

In some embodiments of the invention, the capsules are provided at or near an outer surface of an expandable medical device. Upon expansion of the device, the capsules are compressed, for example, between the device and the surrounding tissue. By selecting capsules having critical pressures that are less than or equal to the pressures that are generated during expansion of the device, therapeutic agents (or other agents) are released.

As a specific example, capsules having walls that contain up to 24 alternating layers of PAH and PSS have been reported, in which each double layer of PSS/PAH has a thickness of about 4 nm. See, e.g., C. Gao et al., "Elasticity of hollow polyelectrolyte capsules prepared by the layer-by-layer technique," Eur. Phys. J. E 5, 21-27 (2001). These capsules were further reported as having radii on the order of 2 to 4.3 microns and as having elastic moduli on the order of 500 Mpa. Taking as a specific example a spherical capsule having a radius of 2 microns with ten PSS/PAH double layers (thus having a wall thickness of 40 nm), this capsule can be predicted, using the above equation, to collapse at about $8 \times 10^5 N/m^2$, or 8 bar. This pressure is within the pressure range that is commonly encountered during expansion of vascular stents, or during the performance of percutaneous transluminal angioplasty (PTA) or percutaneous transluminal coronary angioplasty (PTCA) procedures. As a result, by providing such capsules (with encapsulated therapeutic agent inside) at or near the outer surface of the stent or balloon, therapeutic agent is released into surrounding tissue during these procedures.

The capsules can be associated with the medical devices in any number of ways. As indicated above, in many embodiments, the capsules are disposed at or near an outer surface of an expandable medical device, such as a balloon or stent, ultimately releasing their contents under the pressure generated by the device.

The capsules can be disposed at or near the outer surface of the device via a number of approaches.

In some embodiments, the capsules are embedded in a coating at or near an outer surface of the medical device. For instance, a polymer solution can be provided by dissolving a polymer in a solvent, which does not dissolve the capsules. A dispersion of the capsules within such a polymer solution is then be applied to a medical device, for example, by spraying, dipping, and so forth. Solvent evaporation produces a coating in which the capsules are embedded within the polymer. As a specific example, drug-containing capsules having a PAH/PSS polyelectrolyte coating can be mixed with either (a) a solution of polystyrene-polyisobutylene block copolymer (see, e.g., U.S. Pat. Appln. No. 20020107330, which is hereby incorporated by reference in its entirety, which describes a polystyrene-polyisobutylene-polystyrene triblock copolymer, among others) in toluene, or (b) a solution of pellethane thermoplastic polyurethane elastomer (available from Dow Chemical Co.) in toluene. (Note that capsules having PAH/PSS polyelectrolyte coatings are stable in toluene, as well as a number of other organic solvents.) The resulting dispersion is then applied to a medical device surface to provide a coating with embedded capsules as described above.

As another example, a medical device can be provided with a layer that comprises capsules embedded within a hydrogel. Hydrogels are typically hydrophilic polymeric materials that have the ability to absorb large amounts of water or other polar molecules, up to many times the weight of the hydrogel itself. Hydrogels have been disclosed as coatings for implantable or insertable medical devices or as materials for constructing the device itself in, for example, U.S. Pat. Nos. 6,316,522; 6,261,630; 6,184,266; 6,176,849; 6,096,108; 6,060,534; 5,702,754; 5,693,034; and, 5,304,121, each of which is assigned to Boston Scientific Corporation or SciMed Life Systems, Inc. and is incorporated herein in its entirety by reference. Hydrogels, such as those described in the foregoing exemplary U.S. Patents, can be based on synthetic or naturally occurring materials, or a composite thereof; can be biodegradable or substantially non-biodegradable; and, can be modified or derivatized in numerous ways to render the hydrogel more suitable for a desired purpose. For example, the hydrogel can be modified by chemically cross-linking with, for example, a polyfunctional cross-linking agent that is reactive with functional groups covalently bonded to the polymer structure. The hydrogel polymer can also be ionically cross-linked with, for example, polyvalent metal ions. Many hydrogel polymers can be both chemically and ionically cross-linked. Examples of hydrogel polymers include polyacrylates; poly(acrylic acid); poly(methacrylic acid); polyhydroxyethyl methacrylates; polyacrylamides; poly(N-alkylacrylamides); polyalkylene oxides; poly(ethylene oxide); poly(propylene oxide); poly(vinyl alcohol); polyvinyl aromatics; poly(vinylpyrrolidone); poly(ethyleneimine); polyethylene amine; polyacrylonitrile; polyesters; polyvinyl sulfonic acid; polyamides; poly(L-lysine); hydrophilic polyurethanes; maleic anhydride polymers; proteins; fibrin; collagen; cellulosic polymers; methyl cellulose; carboxymethyl cellulose; dextran; carboxymethyl dextran; modified dextran; alginates; alginic acid; pectinic acid; hyaluronic acid; chitin; pullulan; elastin; laminin; agarose; gelatin; gellan; xanthan; carboxymethyl starch; chondroitin sulfate; guar; starch; and copolymers, mixtures and derivatives thereof.

Figure 1B:
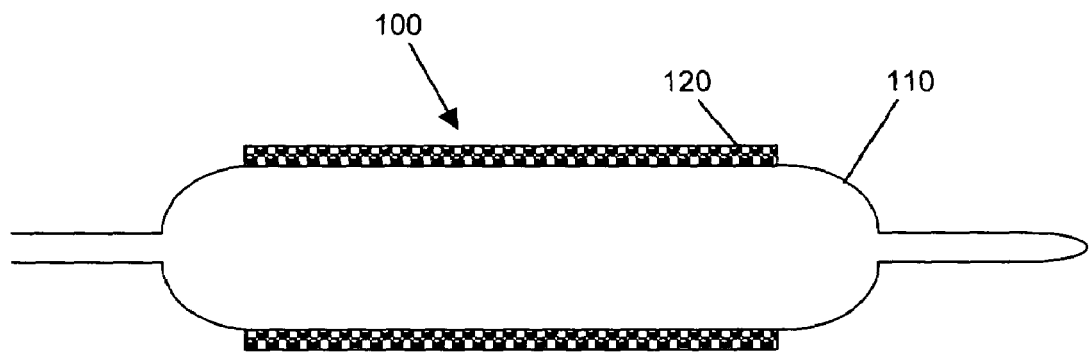
FIG. 1B is a schematic illustration of the balloon catheter of FIG. 1A, post-inflation, in accordance with an embodiment of the invention.

One specific embodiment of the invention is illustrated in FIG. 1A, which contains a schematic representation of a balloon catheter 100. The balloon catheter 100 comprises a balloon 110 that that is modified by the addition of a layer 120, which comprises capsules admixed with a polymer. The balloon catheter is adapted for insertion into a body lumen. Once a site of interest is reached (e.g., a atherosclerotic lesion), the balloon 110 is inflated as illustrated in FIG. 1B, compressing the layer 120 against the surrounding tissue (not shown). During balloon expansion, the pressure that is exerted upon the capsules within the layer 120 eventually reaches the critical pressure associated with the capsules, at which point the therapeutic agent is released.

In other embodiments of the present invention, the capsules are attached to the medical device surface using any of a variety of schemes, for example, ionic bonding, covalent bonding, hydrogen bonding, Van der Waals bonding, bonding through hydrophilic/hydrophobic interactions, bonding through antibody-antigen interactions, bonding via nucleic hybridization techniques, bonding via magnetic fields, and so forth.

For example, the surface of the medical device can be provided with an outer layer of polyelectrolyte that is opposite in charge to the outer polyelectrolyte layer that is provided on the capsules, resulting in ionic attachment of the capsules to the device. For instance, a stent can be used as a template for a single polyelectrolyte layer (or any number of alternating oppositely charged polyelectrolyte layers). If desired, an electrical potential can be applied to the stent while it is immersed in a polyeletrolyte solution to promote adsorption of the initial polyelectrolyte layer. Once an initial polyelectrolyte layer is established, subsequent polyelectrolyte layers, each with a charge opposite to that of the prior layer, can be deposited as discussed above. As with the capsules, the surface charge of the stent is changed to the opposite electrical charge with each deposited polyeletrolyte layer. The final layer on the medical device and the final layer of the capsules should have opposite charges. For example, the stent can be provided with an outer layer of PAH, while the capsules can be provided with an outer layer of PSS.

As another example, capsules can be magnetically held in place on the medical device surface. For example, capsules can be provided as described above, which are either magnetic (e.g., capsules that contain magnetic powder) or are susceptible to magnetic fields (e.g., capsules that contain a paramagnetic material, such as iron powder). These capsules can then be attached to the medical device, for instance, by virtue of the medical device (a) having a magnetic field (e.g., because it comprises a permanent magnet or electromagnet), in which case both magnetic and paramagnetic capsules will be attracted, or (b) containing one or more paramagnetic materials such as iron, in which case magnetic capsules will be attracted.

In still other embodiments, the capsules are mechanically held in place at or near the medical device surface. As one example, cavities can be provided in the surface of a medical device (e.g., indentations/holes can be provided in an outer hydrogel layer), and the capsules can be provided within the cavities.

In other instances, the capsules are mechanically held between two components of the medical device, which results in compression of the capsules upon activation of the device. For example, the capsules can be provided between an outer porous layer and an inner expandable balloon. Upon expansion of the inner balloon, the capsules are compressed against the outer porous layer, releasing the therapeutic agent from the capsules. The therapeutic agent exits the device by passing through the porous layer.

In many embodiments of the invention, fluid inflation is used to apply pressure to the capsules. However, essentially any mechanism can be used to apply pressure to the capsules, so long as critical pressure can be generated.

For example, in some embodiments of the invention, a medical device comprising an electroactive polymer (EAP) actuator is utilized. EAP-actuated medical devices for use in connection with the present invention can be constructed, for example, using (a) an electroactive polymer layer such as a layer comprising polypyrrole, polyaniline, polysulfone, polyacetylene, and so forth, adjacent to (b) a conductive layer, such as a metal foil (e.g., gold foil, silver foil, etc.), a conductive polymer layer (e.g., a polymer layer having a conductive carbon coating), carbon nanotube paper (sometimes referred to as "bucky paper"), and so forth. A device based on this type of construction is manufactured by Micromuscle AB, Linkoping, Sweden. When activated, the stent shrinks. When deactivated, the stent expands. Thus, once the stent is placed inside a body lumen, for example, a blood vessel, and electrical connection to an applied voltage source is broken, the device expands into contact with the vessel. Other EAP-actuated devices are known that can be used for the practice of the present invention, including EAP-actuated expanding catheters. See, e.g., U.S. Pat. No. 5,855,565, the disclosure of which is hereby incorporated by reference.

In various embodiments of the present invention, capsules are provided at or near the outer surface of an EAP-actuated medical device. The capsules can be provided at or near the surface of the EAP-actuated device using a variety of techniques, including those previously discussed. After the medical device is inserted into a patient and after the device reaches a site of intended drug release, the device is deployed, subjecting the capsules to critical pressure and releasing therapeutic agent.

As noted above, capsules can be provided which encapsulate a single agent. Alternatively, capsules can be provided which encapsulate multiple agents. For example, first and second drugs can be provided within a single capsule core. As another example, a first drug can be provided in the capsule core, an inner multilayer encapsulation can surround the core, an additional layer containing a second drug can then be provided over the inner multilayer encapsulation, and an outer multilayer encapsulation can then be provided over the layer containing the second drug.

Moreover, two or more populations of capsules, each containing different agents, can be combined within a single medical device. For example, in certain embodiments, a first capsule population containing a first drug (e.g., heparin, Vitamin A, or urokinase) can be provided which has a lower associated critical pressure than that of a second capsule population containing a second drug (e.g., an anti-restenosis drug such as placitaxel, sirolimus, everolimus, or tacrolimus). As a result, a medical device containing both populations of capsules can be initially activated to exert a pressure sufficient to release the first drug from the first population of capsules. After a predetermined pause, if any, the medical device can be further activated to exert a pressure sufficient to release the second drug from the second population of capsules.

A wide range of capsule loading levels can be used in connection with the medical devices of the present invention, with the amount of capsule loading being readily determined by those of ordinary skill in the art and depending, for example, upon the condition to be treated, the nature of the therapeutic agent, the administration scheme, and so forth.

Although various embodiments are specifically illustrated and described herein, it will be appreciated that modifications and variations of the present invention are covered by the above teachings without departing from the spirit and intended scope of the invention.

The invention claimed is:

1. A medical device comprising a plurality of capsules, said capsules comprising a therapeutic agent and a multilayer polyclectrolyte shell, wherein said medical device is adapted to apply a pressure to said capsules that is greater than or equal to the critical pressure of at least a portion of said capsules such that therapeutic agent is released from said capsules upon rupture of said capsules, wherein at least a first portion of said capsules comprise a first therapeutic agent and have a first critical pressure, wherein at least a second portion of said capsules comprise a second therapeutic agent and have a second critical pressure, and wherein said second critical pressure is greater than said first critical pressure.

2. A medical procedure comprising: inserting the medical device of claim 1 into a patient; and activating said medical device to apply a pressure to said capsules that is greater than or equal to said first critical pressure and less than said second critical pressure such that said first therapeutic agent is released; and (d) further activating said medical device to apply a pressure to said capsules that is greater than or equal to said second critical pressure such that said second therapeutic agent is released.

3. A stent comprising a plurality of capsules, said capsules comprising a therapeutic agent and a multilayer polyelectrolyte shell, wherein said stent is adapted to apply a pressure to said capsules that is greater than or equal to the critical pressure of at least a portion of said capsules such that therapeutic agent is released from said capsule, and wherein said stent comprises an electroactive polymer actuator.

4. A medical device comprising a plurality of capsules, said capsules comprising a therapeutic agent and a multilayer polyelectrolyte shell, wherein said medical device is adapted to apply a pressure to said capsules that is greater than or equal to the critical pressure of at least a portion of said capsules such that therapeutic agent is released from said capsules, wherein said medical device is an expandable catheter that comprises an electroactive polymer actuator.

* * * * *